(12) United States Patent
Ogliari et al.

(10) Patent No.: US 8,835,527 B2
(45) Date of Patent: Sep. 16, 2014

(54) DENTAL COMPOSITION COMPRISING A CALCIUM SOURCE

(75) Inventors: Fabrício Aulo Ogliari, Pelotas (BR); Evandro Piva, Pelotas (BR); Valdemir dos Santos, Ibiporã (BR); Roberto Queiróz Martins Alcântara, Londrina (BR); César Eduardo Bellinati, Londrina (BR)

(73) Assignee: Angelus Industria de Produtos Odontologicos S/A, Lindoia, Londrina, PR (BR)

( * ) Notice: Subject to any disclaimer, the term of this patent is extended or adjusted under 35 U.S.C. 154(b) by 0 days.

(21) Appl. No.: 13/557,435

(22) Filed: Jul. 25, 2012

(65) Prior Publication Data

US 2013/0023601 A1    Jan. 24, 2013

Related U.S. Application Data

(63) Continuation-in-part of application No. PCT/BR2011/000027, filed on Jan. 25, 2011.

(30) Foreign Application Priority Data

Jan. 25, 2010 (BR) .................................... 1001878

(51) Int. Cl.
| | | |
|---|---|---|
| *A61K 6/087* | (2006.01) | |
| *C08L 63/00* | (2006.01) | |
| *C08L 79/00* | (2006.01) | |
| *A61K 8/02* | (2006.01) | |
| *A61K 6/00* | (2006.01) | |
| *A61K 6/02* | (2006.01) | |
| *A61K 6/06* | (2006.01) | |

(52) U.S. Cl.
CPC ............... *A61K 6/0038* (2013.01); *A61K 6/087* (2013.01); *A61K 6/0005* (2013.01); *A61K 6/023* (2013.01); *A61K 6/0067* (2013.01); *A61K 6/0073* (2013.01); *A61K 6/0606* (2013.01)

USPC ........................................................ 523/116

(58) Field of Classification Search
None
See application file for complete search history.

(56) References Cited

U.S. PATENT DOCUMENTS

| | | | | |
|---|---|---|---|---|
| 3,047,408 | A * | 7/1962 | Dougherty ...................... | 106/35 |
| 3,066,112 | A * | 11/1962 | Bowen ......................... | 523/116 |
| 3,179,623 | A * | 4/1965 | Bowen ......................... | 528/205 |
| 3,194,784 | A * | 7/1965 | Bowen ......................... | 523/116 |
| 3,751,399 | A * | 8/1973 | Lee, Jr. et al. .................... | 26/232 |
| 3,926,906 | A * | 12/1975 | Lee et al. ....................... | 523/116 |
| 4,240,832 | A * | 12/1980 | Jandourek ....................... | 106/35 |
| 5,276,068 | A * | 1/1994 | Waknine ........................ | 522/28 |
| 5,348,988 | A * | 9/1994 | Suh et al. ....................... | 523/118 |
| 5,408,022 | A * | 4/1995 | Imazato et al. ............... | 526/259 |
| 5,415,547 | A * | 5/1995 | Torabinejad et al. ...... | 433/228.1 |
| 5,444,104 | A * | 8/1995 | Waknine ........................ | 522/24 |
| 5,733,949 | A * | 3/1998 | Imazato et al. ............... | 523/109 |
| 6,326,417 | B1 * | 12/2001 | Jia ................................ | 523/116 |
| 6,455,608 | B1 * | 9/2002 | Jia et al. ......................... | 523/115 |
| 2002/0045678 | A1 * | 4/2002 | Lopez et al. ................... | 523/116 |

OTHER PUBLICATIONS

Grind Gauge and Blaine Number Conversion Chart, http://www.geohawleyminerals.com/Resources/ParticleSizeConversions.htm, date downloaded Oct. 20, 2013.*

* cited by examiner

*Primary Examiner* — James J Seidleck
*Assistant Examiner* — Peter A Salamon
(74) *Attorney, Agent, or Firm* — Vedder Price P.C.; Thomas J. Kowalski; Deborah L. Lu

(57) ABSTRACT

The present invention relates to cements useful in dental applications, and more particularly to dental compositions which may release calcium ions, which may comprise at least one of salicylic acid ester derivative and a calcium source. The present invention further relates to the use of at least one of salicylic acid ester derivative and a calcium source for producing a dental composition, having biological properties and which may release calcium ions for use in dental procedures of intermediate restorations and channel filling.

2 Claims, 1 Drawing Sheet

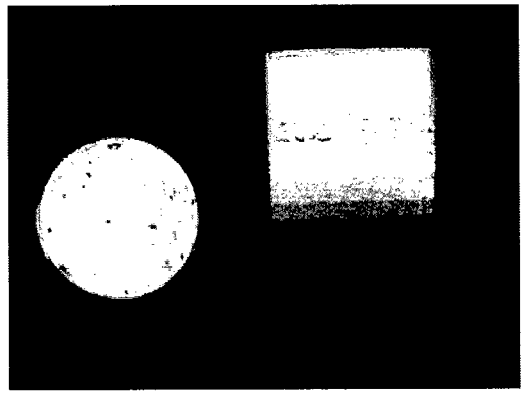

US 8,835,527 B2

DENTAL COMPOSITION COMPRISING A CALCIUM SOURCE

RELATED APPLICATIONS AND INCORPORATION BY REFERENCE

This application is a continuation-in-part application of international patent application Serial No. PCT/BR2011/000027 filed 25 Jan. 2011, which published as PCT Publication No. WO 2011/088540 on 28 Jul. 2011, which claims benefit of Brazilian patent application Serial No. PI 1001878-6 filed 25 Jan. 2010.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to cements useful in dental applications, and more particularly to dental compositions which release calcium ions.

In particular, the present invention relates to dental compositions which may comprise at least one salicylic acid ester derivative and a calcium source.

The present invention further relates to the use of at least one of salicylic acid ester derivative and a calcium source for producing dental compositions which release calcium ions for use in dental procedures and intermediate restorations of channel filling.

BACKGROUND OF THE INVENTION

Caries is a process caused by bacteria that leads to the destruction of dental tissues and can result in tooth loss if not treated in due time. The demineralization of dental tissues (enamel, dentin or cement) is caused by acids produced by bacterial fermentation of food residues in the diet, especially sugars. The presence of the acids lowers the pH and causes the dissolution of enamel and transport of calcium and phosphate into the oral environment.

Once installed, the evolution of caries can be divided into three phases. In the first phase, the caries affects only the enamel; in a second phase, it deepens and enters the dentin; in the third stage, it reaches the root channel. In the second, and especially in the third phase, toothache starts caused mainly by inflammation due to bacterial aggression.

In order to prevent the carious process and restore the tooth's normal function, various techniques and procedures that make use of different materials are used in the treatment of caries. After the diagnosis of caries, the first step is the partial or total removal of carious tissue followed by the steps of pulp protection (artery, veins and nerves) and definitive restoration of tooth. For tooth restoration, basically two materials are used. The first material, used internally (intermediate restorative material), has biological properties that protect the pulp. The second material, used externally, restores the outer shape of the tooth and is called definitive restorative material. The protection of the pulp with intermediate restorative material, prior to the final restorative material, is needed because definitive restorative materials do not have the necessary biological properties required to protect the pulp and in fact are usually aggressive to the pulp. Desirably these intermediate materials have the ability to create an unsuitable environment for bacterial growth, and additionally induce the repair of the pulp and the remaining dentin.

Nevertheless, when there is a delay in seeking treatment, to the point that the carious process invades the radicular channel and bacteria cause the destruction of the arteries, veins and nerves, it is necessary to undergo root channel treatment. This treatment is performed in three stages: removal of dental pulp, debridement of the channel walls to remove the bacteria adhered thereto, and finally filling the channel with a filling material. It is highly desirable that this filling material is able to promote an efficient sealing of the root channel and preferably that it also acts as an antibacterial and promotes remineralization.

The common products used as protectors of the dental pulp (artery, veins and nerves) as intermediate material prior to definitive restoration or as channel filling materials contain calcium hydroxide in their formulations. Calcium hydroxide has three important properties for dental treatment. Firstly, calcium hydroxide is capable of neutralizing the acidic components (that dissolve dental tissues) produced by bacteria. Secondly, calcium hydroxide makes the environment unsuitable for bacterial growth (making it highly alkaline). Finally, calcium hydroxide induces the formation of dentin and bone, recovering the regions damaged by acids from bacteria. However, calcium hydroxide has a high solubility in slightly wet environments, which makes its use as a calcium ion source disadvantageous in cases where product stability over time is required.

Over the years several formulations based on calcium hydroxide have been used to treat dental cavities caused by caries. Formulations are usually aqueous or in the form of pastes, which means that although they have the ability to release calcium, they are not adequately resistant to withstand the compression of the definitive restorative material and the masticatory load.

The first report of a cement with properties similar to the present invention, that is, the ability to release calcium and good mechanical strength was made by Wheeler in the U.S. Pat. No. 2,516,438. This document describes compositions presented in a powder/liquid form, wherein the powder consists mainly of calcium hydroxide and the liquid of eugenol. According to the author, the composition would be a suitable capping material for the pulp. However, this invention occurred before the onset of restorative materials based on methacrylates, which polymerize in the presence of free radicals. Since it is widely known that eugenol has the ability to inhibit the radical polymerization of these resin materials, the use of eugenol combined with restorative materials based on methacrylates, is thus currently contraindicated. Additionally, the invention described in U.S. Pat. No. 2,516,438 uses calcium hydroxide as a calcium source, that, as previously described, has an excessive solubility, affecting the integrity of the material over time.

In an attempt to overcome the deficiencies of the aqueous compositions or compositions containing organic solvents (for example, eugenol), U.S. Pat. No. 3,047,408 relates to a composition containing a mixture of calcium hydroxide in excess with a polyhydric alcohol and salicylic acid esters in a powder/liquid form. This mixture reacts to form a permeable and rigid mass of calcium phenolate, having free calcium hydroxide dispersed therein. With this composition, a material with calcium ion release capacity, without the disadvantageous need of using eugenol, was obtained. However, the invention still has the limitation of having calcium hydroxide as a calcium source, compromising the material's performance over time due to its high solubility in humid environments.

U.S. Pat. No. 4,240,832 relates to a composition in a paste-paste form, based on calcium hydroxide and a salicylic acid ester based resin. Despite the advantageous paste-paste presentation, the salicylate resin used (or salicylic acid ester resin) is the condensation product of methyl salicylate with paraformaldehyde, which presents serious environmental and occupational risks during their production.

Subsequently, U.S. Pat. No. 5,922,785 also relates to a composition in a paste-paste form, based on calcium hydroxide and salicylate resin. Advantageously, said invention does not use aldehydes in the synthesis of salicylate resin, making the process safer. However, it still has the disadvantage of using calcium hydroxide as a calcium ion source.

U.S. Pat. No. 5,415,547 also relates to a repair material for dental structures which is able to release calcium ions based on Portland cement. Despite using a more suitable calcium source, the adherence of the cement depend on its mixture with water, resulting in a material with very weak mechanical properties, and having only indication limited in situations where there is no requirement for mechanical strength during its use.

Citation or identification of any document in this application is not an admission that such document is available as prior art to the present invention.

OBJECTIVES OF THE INVENTION

There is a need for obtaining a material with ideal characteristics for use as an intermediate restorative material and/or as a filling material. In order to meet such requirements, the use of a low solubility calcium source that allows greater mechanical strength as well as a salicylate-based resin capable of forming a permeable ionic polymer is needed.

In view of the above, the present invention has the objective of providing cements useful for dental applications, more particularly dental compositions which may release calcium ions.

It is a specific objective of the present invention to provide dental compositions which may comprise at least one of salicylic acid ester derivative and a low solubility calcium source.

It is another objective of the present invention to provide the use of at least one salicylic acid ester derivative and a calcium source for producing a dental composition, having biological properties and potential for releasing calcium ions for use in dental procedures, such as intermediate restorations and channel filling, having the ability to release calcium ions in a controlled manner, without undergoing structural changes as those presented when calcium hydroxide is used as ion source. Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWING

The following detailed description, given by way of example, but not intended to limit the invention solely to the specific embodiments described, may best be understood in conjunction with the accompanying drawings.

FIG. 1 shows a radiography of a sample of a preferred embodiment of the dental cement described in the present invention, with a diameter of 10 mm and height of 1 mm. The radiographic film presents a sample of this cement placed next to an aluminum scale ranging from 0.5 mm to 5 mm.

FIG. 1 is part of this specification and is included herein to illustrate certain aspects of the invention. The object of this invention can be better understood with reference to this FIGURE, in combination with the detailed description of the preferred embodiment presented herein.

DETAILED DESCRIPTION OF THE INVENTION

The present invention relates to dental compositions which may comprise at least one of salicylic acid ester derivative and a calcium source. The dental compositions of the present invention are suitable for intermediate restorations and channel filling.

Preferably, the material of the present invention consists of two components in the form of two pastes, although it is also possible in the powder form. The first paste has mainly a calcium source and a resin. This resin should be preferably inert, but may also be reactive, preferably based on epoxides or amines. The second paste is formed by at least one derivative of salicylic acid ester. More preferably, for product stability, the calcium source and the salicylic acid ester derivative are placed in separate compartments.

The calcium source used in the materials of the present invention is preferably mineral trioxide aggregate, widely known by the acronym MTA. This aggregate consists essentially and preferably of three major components: Alite ($3CaO.SiO_2$) belite ($2CaO.SiO_2$) and tricalcium aluminate ($3CaO.Al_2O_3$). Additionally in another embodiment of the present invention, a fourth component may be added, tetracalcium ferroaluminate ($4CaO.Al_2O_3.Fe_2O_3$).

Preferably, during the burning of the raw materials in order to form the mentioned phases, there is further the presence of free CaO in low concentration. These components have the ability to release calcium ions in a controlled manner, without undergoing the severe structural changes presented when calcium hydroxide is used as the ion source. Thus, a gradual and long-term calcium ion release system is possible, which is a highly desirable characteristic of the materials of the present invention.

In a preferred embodiment of the present invention, MTA will be available in a paste form by mixing its mixture with inert plasticizer resins, such as, but not restricted to the following materials: epoxy derivatives, methacrylate derivatives, sulfonamide-based resins, vegetable resins, glycol resins, resins based on polyesters and polyethers.

Moreover, in another embodiment of the present invention, Portland cement may be used alternately as a calcium source in the paste formulation described above.

The salicylic acid ester(s)-based resin is preferably present in the second component of the material and a great variety of salicylic acid esters or a mixture thereof may be used.

For adjusting the rheology, microparticulated and nanoparticulated inorganic particles of different metal oxides may be preferentially incorporated into both pastes.

Another way for obtaining rheology adjustment is by using organic thickening agents, such as various types of resins, gums, fibers, among other thickening agents.

An important feature of the material for its application is the radiopacity, that is, the material's ability to block X-rays used in a radiological examination. To provide this property to the materials and compositions of the present invention, various radiopacifiers agents may be used, such as, but not restricting to barium, bismuth, rare earths, strontium, zirconium, silicon, aluminum, titanium, tungsten, among other agents radiopacifiers.

Although the present invention and its advantages have been described in detail, it should be understood that various changes, substitutions and alterations may be made herein without departing from the spirit and scope of the invention as defined in the appended claims.

The present invention will be further illustrated in the following Examples which are given for illustration purposes only and are not intended to limit the invention in any way.

EXAMPLES

In order to provide a better understanding of the present invention and clearly demonstrate the technical advances achieved by the present invention, the results of different experiments carried out with respect to this invention are presented herein as examples.

Tests to characterize the performance of the material were carried out according to the standard ISO 6876.

These examples are presented merely for illustrative purposes and should not in any way be considered limitative to the scope and range of the present invention.

Example 1

Synthesis of the Disalicylate Resin (Salicylate Ester) by Transesterification 0.5 mol of 1.3-butyleneglycol and 1.1 mol of methyl salicylate were added in a 500 mL flask. The mixture was heated to 110° C. and kept at this temperature for 30 minutes under constant stirring. 10 mmol of titanium isopropoxide was added and the reaction temperature increased to 200° C., with continuous removal of the methanol generated as byproduct of transesterification.

Example 2

Paste Formulation

According to the potential applications of the present invention and merely for illustrative purposes, without intending to limit in any way the scope of the present invention, one of the possible formulations, based on MTA, is described below:

| Component | Concentration range (%) | Preferred composition (%) |
|---|---|---|
| Base Paste | | |
| Disalicylate resin | 10-50 | 38.2 |
| Bismuth oxide | 30-80 | 60.5 |
| Titanium dioxide | 0.1-10 | 1.3 |
| Total | | 100.0 |
| Catalyst past | | |
| MTA | 10-50 | 39.5 |
| n-ethyl-p,o-toluene sulfonamide | 30-80 | 60 |
| Titanium dioxide | 0.1-10 | 0.5 |
| Total | | 100.0 |

Example 3

Material Performance: Flow

The material was prepared by adding equal parts of the two pastes, and manipulated until the homogenization of the mixture (approximately 10 seconds). Subsequently, 0.05 mL of cement was placed in the center of a glass plate and covered with another glass plate and a 100 g weight was placed on top and kept for 10 minutes. After that time, the weight was removed and the major and minor diameters were measured in the material, resulting in an average corresponding to the material flow capacity.

Results of Flow Analysis:

Flow readings obtained from each sample of the material under discussion and the respective flow diameter averages:

| Sample | Ø1 (mm) | Ø2 (mm) | Ø3 (mm) | ØMean (mm) |
|---|---|---|---|---|
| 1 | 28 | 27 | 25 | 26.66 |
| 2 | 28 | 26 | 29 | 27.66 |
| 3 | 28 | 27 | 26 | 27.00 |

Ø: diameter;
mm: millimeter
Minimal mean diameter established by ISO 6876: 20 mm Example 4

Material Performance: Working Time

The material was prepared by adding equal parts of the two pastes, manipulated for different times (10 seconds, 10 minutes, 20 minutes, 30 minutes, 40 minutes and 50 minutes), according to the table below. Subsequently, similarly to the procedure performed in the flow evaluation, 0.05 mL of cement was placed in the center of the glass plate, covered with another glass plate and a 100 g weight was placed on top and left for 10 min. The flow was checked with the aid of a digital caliper. The working time was determined when the diameter of the cement was 10% lower than the initial diameter (of the cement manipulated during 10 seconds).

Results of Working Time Analysis:

Readings of flow diameter obtained at different times of handling the material and their respective means of major and minor diameter.

| Times | Analysis | | | | |
|---|---|---|---|---|---|
| | Ø1 (mm) | Ø2 (mm) | Ø3 (mm) | Ø4 (mm) | Ø Mean |
| 10 s | 28.41 | 28.36 | 26.67 | 27.39 | 27.54 |
| 10 min | 26.34 | 26.08 | 25.92 | 26.27 | 26.13 |
| 20 min | 26.32 | 25.87 | 25.85 | 26.31 | 26.85 |
| 30 min | 25.99 | 26.78 | 26.01 | 26.21 | 26.38 |
| 40 min | 20.72 | 22.02 | 21.61 | 20.58 | 21.30 |
| 50 min | 16.61 | 16.82 | 15.98 | 16.09 | 16.40 |

Ø: diameter;
mm: millimeter;
s: seconds;
min: minutes.

Example 5

Material Performance: Film Thickness

The combined thickness of two glass plates in contact with a digital micrometer was measured. Then a portion of cement previously handled was deposited in the center of one of the glass plates, covered with another glass plate and then placing a 150 N (15 Kg) weight upon the center of the plate. The material completely filled the space between the glass plates after ten minutes and the thickness of two glass plates with the cement film inside was measured with the aid of a micrometer.

Results of Film Thickness Analysis:

Data collected in the film thickness analysis and averages obtained:

| Measurements | 1 | 2 | 3 |
|---|---|---|---|
| Plate Measurements | 9,380 | 9,380 | 9,273 |
| Plate + Material Measurements | 9,422 | 9,422 | 9,314 |
| Film Thickness | 36 μm | 42 μm | 41 μm |

Maximum Thickness Accepted by ISO 6876: 50 μm

Example 6

Material Performance: Radiopacity

The cement was put into the mold, covered with a glass slide and kept resting for 2 hours to make a sample with a diameter of 10 mm and height of 1 mm. The cement sample was placed on a radiographic film. Near that to the region, a piece of 0.5 mm to 2.5 mm of aluminum (99% pure and 0.5 mm to 5 mm thick). A radiographic measurement of the cement sample and aluminum scale for comparison was taken. The optical density, and hence, the radiopacity of said material in dentistry was determined, as shown in FIG. 1.

Results of the Radiopacity Analysis:

The value of the optical density of the cement image sample should be equal or superior to that found in the range of aluminum corresponding to a thickness of 3 mm. The software Image J was used to calculate the optical density in pixels and the tested cement presented an optical density 77% higher than that presented by the aluminum scale having a thickness of 3 mm.

The invention is further described by the following numbered paragraphs:

1. Dental composition characterized in that it comprises at least one of salicylic acid ester derivative and a calcium source, wherein said calcium source is different from calcium hydroxide.

2. Dental composition, according to paragraph 1, characterized in that it is presented as two distinct components, one comprising at least one of salicylic acid ester derivative and another comprising a calcium source.

3. Dental composition, according to paragraph 2, characterized in that said components are presented as pastes.

4. Dental composition, according to any one of paragraphs 1 to 3, characterized in that the calcium source comprises tricalcium silicate ($3CaO.SiO_2$), dicalcium silicate ($2CaO.SiO_2$) tricalcium aluminate ($3CaO.Al_2O_3$) and calcium oxide (CaO).

5. Dental composition, according to any one of paragraphs 1 to 3, characterized in that the calcium source comprises Portland cement.

6. Dental composition, according to any one of paragraphs 4 or 5, characterized in that the calcium source additionally comprises tetracalcium ferroaluminate ($4CaO.Al_2O_3.Fe_2O_3$).

7. Dental composition, according to any one of paragraphs 1 to 6, characterized in that the calcium source is presented in the form of a finely divided powder.

8. Dental composition according to any one of paragraphs 1 to 7, characterized in that the calcium source is dispersed in an inert resin.

9. Dental composition, according to paragraph 8, characterized in that the inert resin is selected from the group comprising epoxy derivatives, methacrylate derivatives, sulfonamide-based resins, plant resins, glycol resins and polyester and polyether-based resins.

10. Dental composition, according to any one of paragraphs 1 to 7, characterized in that the calcium source is dispersed in a reactive resin.

11. Dental composition, according to paragraph 10, characterized in that the reactive resin is selected from the group comprising epoxide base or amines.

12. Dental composition, according to any one of paragraphs 1 to 3, characterized in that the component of salicylic acid ester is comprised in a resin.

13. Dental composition, according to paragraph 12, characterized in that said resin based on salicylic acid ester comprises one or more salicylic acid esters or a mixture thereof.

14. Dental composition according to any one of paragraphs 12 or 13, characterized in that said salicylic acid ester is methyl salicylate.

15. Dental composition, according to any one of paragraphs 1 to 14, characterized in that the component responsible for curing the material comprises carboxylic acid molecules with different molecular weights.

16. Dental composition, according to any one of paragraphs 1 to 15, characterized in that the component responsible for curing the material comprises epoxide groups.

17. Dental composition, according to any one of paragraphs 1 to 16, characterized in that the component responsible for curing the material comprises amine functional groups.

18. Dental composition, according to any one of paragraphs 1 to 17, characterized in that it comprises microparticulated and nanoparticulated inorganic particles of different metal oxides.

19. Dental composition, according to any one of paragraphs 1 to 18, characterized in that it comprises an organic thickening agent.

20. Dental composition, according to paragraph 19, characterized in that the organic thickening agent is selected from the group consisting of: gums, resins and fibers.

21. Dental composition, according to any one of paragraphs 1 to 3, characterized in that it comprises a radiopacifier material.

22. Dental composition, according to paragraph 21, characterized in that said radiopacifier material is selected from the group consisting of: barium, bismuth, rare earths, strontium, zirconium, silicon, aluminum, titanium and tungsten derivatives.

23. Dental composition, according to any one of paragraphs 1 to 22, characterized in that it comprises from 10% to 50% of disalicylate resin, from 30% to 80% of bismuth oxide and from 0.1% to 10% of titanium dioxide in one component, and from 10% to 50% of mineral aggregated trioxide (MTA) from 30% to 80% of n-ethyl-p, o-toluene sulfonamide and from 0.1% to 10% of titanium dioxide in the other component.

24. Dental composition, according to paragraph 23, characterized in that it comprises: 38.2% of disalicylate resin, 60.5% of bismuth oxide and 1.3% of titanium dioxide in one component, and 39.5% of mineral aggregated trioxide (MTA), 60% of n-ethyl-p, o-toluene sulfonamide and 0.5% of titanium dioxide on the other component.

25. Use of at least one of salicylic acid ester derivative and a calcium source, in which said calcium source is different from calcium hydroxide, characterized in that it is used for producing a composition as defined in any one of paragraphs 1 to 24, for use in dental procedures involving intermediate restorations and root channel filling.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A dental composition comprising
   at least one of salicylic acid ester derivative, from 10% to 50% of disalicylate resin, from 30% to 80% of bismuth oxide and from 0.1% to 10% of titanium dioxide in one component, and
   a calcium source, wherein said calcium source is different from calcium hydroxide, from 10% to 50% of mineral aggregated trioxide (MTA) from 30% to 80% of n-ethyl-p, o-toluene sulfonamide and from 0.1% to 10% of titanium dioxide in another component.

2. The dental composition of claim 1, characterized in that it comprises: 38.2% of disalicylate resin, 60.5% of bismuth oxide and 1.3% of titanium dioxide in one component, and 39.5% of mineral aggregated trioxide (MTA), 60% of n-ethyl-p, o-toluene sulfonamide and 0.5% of titanium dioxide in another component.

* * * * *